US010369116B2

(12) United States Patent
Fujiwara et al.

(10) Patent No.: US 10,369,116 B2
(45) Date of Patent: Aug. 6, 2019

(54) PATCH COMPRISING AN ADHESIVE LAYER HAVING A NONFUNCTIONAL SILICONE OIL

(71) Applicant: HISAMITSU PHARMACEUTICAL CO., INC., Tosu-shi, Saga (JP)

(72) Inventors: Yoko Fujiwara, Tsukuba (JP); Takashi Yasukochi, Tsukuba (JP); Yuka Takagi, Tsukuba (JP)

(73) Assignee: HISAMITSU PHARMACEUTICAL CO., INC., Tosu-shi, Saga (JP)

( * ) Notice: Subject to any disclaimer, the term of this patent is extended or adjusted under 35 U.S.C. 154(b) by 0 days.

(21) Appl. No.: 15/554,923

(22) PCT Filed: Feb. 22, 2016

(86) PCT No.: PCT/JP2016/055010
§ 371 (c)(1),
(2) Date: Aug. 31, 2017

(87) PCT Pub. No.: WO2016/140087
PCT Pub. Date: Sep. 9, 2016

(65) Prior Publication Data
US 2018/0085323 A1    Mar. 29, 2018

(30) Foreign Application Priority Data

Mar. 2, 2015  (JP) ................. 2015-040347

(51) Int. Cl.
*A61K 9/70* (2006.01)
*A61K 47/32* (2006.01)
*A61K 47/34* (2017.01)
*A61K 47/12* (2006.01)
*A61K 47/14* (2017.01)
*A61M 35/00* (2006.01)

(52) U.S. Cl.
CPC .......... *A61K 9/7061* (2013.01); *A61K 9/7069* (2013.01); *A61M 35/00* (2013.01); *A61K 47/12* (2013.01); *A61K 47/14* (2013.01); *A61K 47/32* (2013.01); *A61K 47/34* (2013.01)

(58) Field of Classification Search
None
See application file for complete search history.

(56) References Cited

U.S. PATENT DOCUMENTS

| 7,556,823 | B2 * | 7/2009 | Miller, II | A61K 9/7069 424/448 |
| 2003/0060479 | A1 | 3/2003 | Brown et al. | |
| 2004/0142024 | A1 * | 7/2004 | Chono | A61K 9/7053 424/449 |
| 2005/0202073 | A1 | 9/2005 | Jackson et al. | |
| 2014/0083878 | A1 * | 3/2014 | Tang | A61K 9/7061 206/204 |
| 2015/0250877 | A1 | 9/2015 | Umemoto et al. | |

FOREIGN PATENT DOCUMENTS

| JP | 2007-217328 A | 8/2007 |
| JP | 2007-528392 A | 10/2007 |
| JP | 2009-274959 A | 11/2009 |
| WO | 99/26572 A1 | 6/1999 |
| WO | 2008/024408 A2 | 2/2008 |
| WO | 2014/057928 A1 | 4/2014 |

OTHER PUBLICATIONS

International Preliminary Report on Patentability and Written Opinion of the International Searching Authority dated Sep. 14, 2017 in International Application No. PCT/JP2016/055010.
International Search Report of PCT/JP2016/055010 dated Apr. 26, 2016.
Communication dated Jul. 24, 2018 from the European Patent Office in counterpart application No. 16758781.5.

* cited by examiner

*Primary Examiner* — Ernst V Arnold
*Assistant Examiner* — Kyung S Chang
(74) *Attorney, Agent, or Firm* — Sughrue Mion, PLLC

(57) ABSTRACT

A patch includes an adhesive layer and a release liner laminated on at least one surface of a backing. The adhesive layer comprises, as an adhesive base agent, at least one selected from the group consisting of acrylate-based adhesives and rubber-based adhesives, and the adhesive layer comprises 0.3 to 5% by mass of a nonfunctional silicone oil having a kinematic viscosity of 10 to 350 cSt at 25° C.

5 Claims, No Drawings

PATCH COMPRISING AN ADHESIVE LAYER HAVING A NONFUNCTIONAL SILICONE OIL

CROSS REFERENCE TO RELATED APPLICATIONS

This application is a National Stage of International Application No. PCT/JP2016/055010 filed Feb. 22, 2016, claiming priority based on Japanese Patent Application No. 2015-040347 filed Mar. 2, 2015, the contents of all of which are incorporated herein by reference in their entirety.

TECHNICAL FIELD

The present invention relates to a patch, and more specifically relates to a patch in which an adhesive layer and a release liner are laminated on a backing.

BACKGROUND ART

In general, a patch includes an adhesive layer and a release liner on at least one surface of a backing, the release liner being for protecting the adhesive layer before use of the patch. The release liner is desired to be adequately easy to peel off from the adhesive layer. More specifically, if the release liner is difficult to peel off from the adhesive layer, one has a difficulty in using the patch in the process of attaching the patch to the skin, and, in extreme cases, a problem arises in that the adhesive layer peels off from the backing while the release liner remains adhered to the adhesive layer. On the other hand, the release liner in a state excessively easy to peel off from the adhesive layer may move out of alignment with the adhesive layer during manufacturing or storage of the patch, and cause a problem in that the adhesive layer cannot be protected sufficiently by the release liner.

Thus, there have been used so far patches in which what is termed release treatment is applied to the surfaces of release liners in order to improve the releasability of the release liners. Here, in the release treatment, a release agent such as a silicone-based resin or a fluorine-based resin is applied in the form of a layer to the surface of a release liner, and then is fixed by crosslinking or the like.

Meanwhile, Japanese Unexamined Patent Application Publication No. 2009-274959 (PLT 1) states that, in a patch including an adhesive layer containing a silicone-based adhesive as an adhesive base agent, the adhesive layer is blended with a polar silicone oil, and this silicone treatment on the adhesive layer improves the releasability of a release liner.

CITATION LIST

Patent Literature

[PLT 1] Japanese Unexamined Patent Application Publication No. 2009-274959

SUMMARY OF INVENTION

Technical Problem

However, a composition of an adhesive layer is generally determined from the viewpoints of adhesiveness to the skin, transdermal absorbability (skin permeability) and temporal stability of a drug to be contained therein, rather than the releasability from the release liner. Once the basic composition of the adhesive layer is determined from such viewpoints, changing the basic composition in consideration of the releasability from the liner has a high risk of causing a new problem, and therefore is difficult to do. In addition, since the releasability of the release liner tends to deteriorate over time, there is a need to maintain adequate releasability stably over time without changing the basic composition of the adhesive layer.

In recent years, patches each having an adhesive layer containing an acrylate-based adhesive or a rubber-based adhesive as an adhesive base agent have been developed depending on various drugs. Under these circumstances, the present inventors have found it very useful that, without changing the basic composition of such an adhesive layer while having no adverse effects on the adhesiveness to the skin and the transdermal absorbability (skin permeability) and temporal stability of a drug to be contained therein, the releasability from the release liner can be adjusted to an adequate range and furthermore the adequate releasability can be maintained stably over time.

The present invention has been made in view of the aforementioned problems, and has an object to provide a patch which, without changing the basic composition of an adhesive layer containing an acrylate-based adhesive or a rubber-based adhesive as an adhesive base agent, while having no adverse effects on the adhesiveness to the skin and the transdermal absorbability (skin permeability) and temporal stability of a drug to be contained therein, can achieve adjustment of the releasability from the release liner to an adequate range, and also can obtain an ability to maintain the adequate releasability stably over time.

Solution to Problem

As a result of earnest studies to achieve the above-described object, the present inventors have found that when a patch comprising an adhesive layer comprising an acrylate-based adhesive or a rubber-based adhesive as an adhesive base agent comprises 0.3 to 5% by mass of a nonfunctional silicone oil having a kinematic viscosity of 10 to 350 cSt at 25° C., the patch can achieve adjustment of the releasability of the release liner from the adhesive layer to an adequate range, and also obtain an ability to maintain the adequate releasability stably over time, while having no adverse effects on the adhesiveness to the skin and the transdermal absorbability (skin permeability) and temporal stability of a drug to be contained therein, and thus have completed the present invention.

Specifically, the patch of the present invention is a patch comprising an adhesive layer and a release liner laminated on at least one surface of a backing, wherein the adhesive layer comprises, as an adhesive base agent, at least one selected from the group consisting of acrylate-based adhesives and rubber-based adhesives, and the adhesive layer comprises 0.3 to 5% by mass of a nonfunctional silicone oil having a kinematic viscosity of 10 to 350 cSt at 25° C.

In addition, in the patch of the present invention, the adhesive layer preferably further comprises a drug.

Further, in the patch of the present invention, the nonfunctional silicone oil is preferably at least one selected from the group consisting of dimethylpolysiloxane and methylphenylpolysiloxane.

In the patch of the present invention, the adhesive layer preferably further comprises, as a plasticizer, at least one selected from the group consisting of liquid paraffin, liquid polybutene, isopropyl palmitate, isopropyl myristate, diethyl sebacate, and hexyl laurate.

Moreover, in the patch of the present invention, the adhesive layer preferably further comprises, as a transdermal absorption enhancer, at least one selected from the group consisting of fatty acids having a carbon chain of 6 to 20 carbon atoms and aliphatic alcohols having a carbon chain of 6 to 20 carbon atoms.

Further, in the patch of the present invention, the adhesive layer preferably further comprises, as a tackifier, at least one selected from the group consisting of hydrogenated rosin glycerol esters, alicyclic saturated hydrocarbon resins, aliphatic hydrocarbon resins, and terpene resins.

In the patch of the present invention, it is preferable that the adhesive base agent be an acrylate ester-based copolymer, and the adhesive layer further comprise a liquid fatty acid ester and a fatty acid having a carbon chain of 6 to 20 carbon atoms.

Still further, in the patch of the present invention, it is preferable that the adhesive base agent comprise a styrene-isoprene-styrene block copolymer and polyisobutylene, and the adhesive layer further comprise an alicyclic saturated hydrocarbon resin, a petroleum-based oil, a liquid fatty acid ester, and an aliphatic alcohol a carbon chain of 6 to 20 carbon atoms.

Advantageous Effects of Invention

According to the present invention, in a patch in which an adhesive layer and a release liner are laminated on at least one surface of a backing, it is possible to adjust the releasability from the release liner to an adequate range and to maintain the adequate releasability stably over time without changing the basic composition of the adhesive layer comprising an acrylate-based adhesive or a rubber-based adhesive as an adhesive base agent, while having no adverse effects on the adhesiveness to the skin and the transdermal absorbability (skin permeability) and the temporal stability of a drug to be contained therein.

DESCRIPTION OF EMBODIMENTS

Hereinafter, the present invention will be described in detail by preferred embodiments thereof.

A patch of the present invention includes a backing, an adhesive layer laminated on at least one surface of the backing, and a release liner covering the opposite surface of the adhesive layer from the backing.

The above backing may be any backing not particularly limited as far as the backing is generally usable in a patch. Preferably usable materials for the backing include polyesters such as polyethylene terephthalate (PET), polybutylene terephthalate, and polyethylene naphthalate; polyolefins such as polyethylene and polypropylene; nylon; polycarbonate; and metals such as aluminum.

Preferably usable forms of the above backing include a film, a fabric, a foil, a porous sheet, or a laminate thereof.

In the patch of the present invention, the adhesive layer is laminated on at least one surface of the above backing, and the adhesive layer according to the present invention comprises, as an adhesive base agent, at least one selected from the group consisting of acrylate-based adhesives and rubber-based adhesives, and comprises 0.3 to 5% by mass of a nonfunctional silicone oil having a kinematic viscosity of 10 to 350 cSt at 25° C.

The acrylate-based adhesive according to the present invention may be any acrylate-based adhesive not particularly limited as far as the acrylate-based adhesive is generally usable as an adhesive base agent in a patch, and may be, for example, a homopolymer of one alkyl (meth)acrylate, a copolymer of two or more alkyl (meth) acrylates, or a copolymer of an alkyl (meth)acrylate and a comonomer component other than these.

As the above alkyl (meth)acrylate, exemplified are butyl (meth)acrylate, isobutyl (meth)acrylate, hexyl (meth)acrylate, 2-ethylhexyl (meth)acrylate, octyl (meth)acrylate, isooctyl (meth)acrylate, decyl (meth)acrylate, and the like. From the viewpoint of adhesive properties, 2-ethylhexyl (meth)acrylate and octyl (meth)acrylate are preferable, and 2-ethylhexyl (meth)acrylate is more preferable.

Meanwhile, as the above comonomer component, exemplified are 2-hydroxyethyl (meth)acrylate, methacrylic acid, ethylene, propylene, styrene, vinyl acetate, N-vinyl-pyrrolidone, acrylamide, and the like. From the viewpoints that the cohesion of the adhesive can be kept and that the solubility and skin permeability of a drug tend to be better, 2-hydroxyethyl (meth)acrylate, vinyl acetate, and N-vinyl-pyrrolidone are preferable. The above comonomer components may be used alone or in combination of two or more of them.

From the viewpoints that the cohesion of the adhesive can be kept and that the solubility and skin permeability of a drug tend to be better, the acrylate-based adhesive according to the present invention is preferably an acrylic ester-based copolymer such as a copolymer of acrylate ester and vinyl acetate or a copolymer of 2-ethylhexyl acrylic acid and vinylpyrrolidone, and is more preferably a copolymer of acrylate ester and vinyl acetate having an alcoholic hydroxyl group. These acrylate-based adhesives may be used alone or may be used in combination of two or more of them. Specific examples of the acrylate-based adhesives include DURO-TAK 87-2516, DURO-TAK 87-4287, and DURO-TAK 87-2287 (tradenames, manufacture by Henkel AG & Co. KGaA) and the like.

The rubber-based adhesive according to the present invention may be any rubber-based adhesive not particularly limited as far as the rubber-based adhesive is generally usable as an adhesive base agent in a patch and may be, for example, styrene-isoprene-styrene block copolymer (SIS), isoprene rubber, polyisobutylene (PIB), styrene-butadiene-styrene block copolymer (SBS), styrene-butadiene rubber (SBR), natural rubber, or the like. From the viewpoints that the adhesive properties of the rubber-based adhesive and the solubility of a drug tend to be better, SIS and PIB are preferable. These rubber-based adhesives may be used alone or may be used in combination of two or more of them. Specific examples of the rubber-based adhesives include Oppanol B12, B15, B50, B80, B100, B120, B150, B220 (trade names, manufactured by BASF SE); JSR BUTYL 065, 268, 365 (trade names, manufactured by JSR Corporation); VISTANEX LM-MS, MH, H, MML-80, 100, 120, 140 (trade names, manufactured by Exxon Chemical Company); HYCAR (trade name, manufactured by Goodrich Cooperation); STBSTAR T102 (trade name, manufactured by Kaneka Co., Ltd.), and the like.

The content of at least one selected from the group consisting of the acrylate-based adhesives and the rubber-based adhesives and contained as the adhesive base agent in the adhesive layer according to the present invention is not particularly limited, but is 20 to 99% by mass preferably and 30 to 95% by mass more preferably based on the total mass of the adhesive layer (the content of the adhesive base agent is the solid content).

The adhesive layer comprising the above adhesive base agent according to the present invention comprises 0.3 to 5% by mass of a nonfunctional silicone oil having a kinematic viscosity of 10 to 350 cSt at 25° C. Thus, the nonfunctional silicone oil functions as a releasability improver, and therefore enables the releasability from the later-described release liner to be adjusted to an adequate range, and the adequate releasability to be maintained stably over time.

Such a nonfunctional silicone oil means a nonreactive silicone oil that is an oily substance in which siloxane bonds (Si—O—Si) form the main chain, and none of polar functional groups such as polyethylene glycol chain and hydroxyl group, and reactive functional groups (amino group, epoxy group, carbinol group, carboxyl group, mercapto group, and the like) are introduced at side chains or terminals.

As the nonfunctional silicone oil used in the present invention, exemplified are alkylpolysiloxane such as dimethylpolysiloxane and methylethylpolysiloxane, alkylarylpolysiloxane such as methylphenylpolysiloxane, alkylhydrogenpolysiloxane such as methylhydrogenpolysiloxane, and the like. From the viewpoint that the interaction with the drug tends to be less, dimethylpolysiloxane, methylethylpolysiloxane, methylphenylpolysilcxane, and the like are preferable, dimethylpolysiloxane, methylphenylpolysiloxane, and the like are more preferable, and dimethylpolysiloxane is particularly preferable. Such dimethylpolysiloxane is also referred to as methylpolysiloxane or dimethicone, and is an oily substance represented by the following structural formula.

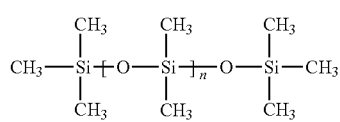

[Chem 1]

Nonfunctional silicone oils in a wide range of viscosity including those having low viscosity (a small molecular weight) to those having high viscosity (a large molecular weight) are used as pharmaceutical and cosmetic raw materials. In the present invention, it is necessary to use a nonfunctional silicone oil whose kinematic viscosity at 25° C. is in a range of 10 to 350 cSt. In a case of using a nonfunctional silicone oil whose kinematic viscosity at 25° C. is less than 10 cSt, the release liner is excessively easy to peel off from the adhesive layer, and may cause a problem in that the adhesive layer cannot be protected sufficiently by the release liner because the release liner moves out of alignment with the adhesive layer during manufacturing or storage of a patch. On the other hand, in a case of using a nonfunctional silicone oil whose kinematic viscosity at 25° C. is more than 350 cSt, the releasability from the release liner is not improved sufficiently, and may cause a problem in that the patch is difficult to use in the process of attaching the patch to the skin because the release liner becomes difficult to peel off from the adhesive layer due to an aging deterioration of the releasability.

Note that, from the viewpoints of enabling the releasability from the release liner to be adjusted to a more adequate range and the adequate releasability to be maintained more stably over time, it is preferable to use a nonfunctional silicone oil whose kinematic viscosity at 25° C. is in a range of 15 to 300 cSt, and more preferable to use a nonfunctional silicone oil whose kinematic viscosity at 25° C. is in a range of 20 to 250 cSt.

Here, the "kinematic viscosity" in this specification means a viscosity measured at 25° C. by using, for example, a capillary viscometer (Ubbelohde type, Cannon-Fenske type, or the like).

In the patch of the present invention, it is necessary to blend 0.3 to 5% by mass of the aforementioned nonfunctional silicone oil based on the total mass of the adhesive layer (the content of the adhesive base agent is the solid content). If the content of the aforementioned nonfunctional silicone oil is less than 0.3% by mass, the releasability from the release liner is not improved sufficiently, and may cause a problem in that the patch is difficult to use in the process of attaching the patch to the skin because the release liner becomes difficult to peel off from the adhesive layer due to an aging deterioration of the releasability. On the other hand, if the content of the aforementioned nonfunctional silicone oil is more than 5% by mass, the adhesive layer is excessively plasticized, resulting in a problem in that the adhesion to the skin deteriorates because a liquid component bleeds out (bleeding occurs) on the surface of the adhesive layer. Moreover, if the content of the aforementioned nonfunctional silicone oil is more than 5% by mass, the release liner is excessively easy to peel off from the adhesive layer, and may cause a problem in that the adhesive layer cannot be protected sufficiently by the release liner because the release liner moves out of alignment with the adhesive layer during manufacturing or storage of a patch.

Note that, from the viewpoints of more surely preventing the occurrence of bleeding while enabling the releasability from the release liner to be adjusted to a more adequate range and the adequate releasability to be maintained more stably over time, the content of the aforementioned nonfunctional silicone oil based on the total mass of the adhesive layer (the content of the adhesive base agent is the solid content) is 0.3 to 4% by mass preferably, and 0.3 to 3% by mass more preferably.

In the present invention, how a nonfunctional silicone oil having a kinematic viscosity of 10 to 350 cSt at 25° C. improves the releasability of the release liner is not really known, the present inventors consider that the presence of a nonfunctional silicone oil having the aforementioned kinematic viscosity produces a specific effect in which an excessive adhesive strength at the interface between the release liner and the adhesive layer can be suppressed stably over time.

In the patch of the present invention, it is more preferable that the aforementioned adhesive layer further comprise a drug (bioactive ingredient), and a solubilizer for the drug to be used and the like may be blended as needed depending on the drug.

In the present invention, a drug preferably blended into the aforementioned adhesive layer may be any drug not particularly limited as far as the drug can be percutaneously absorbed into the body and exert its bioactivity. As such drugs, exemplified are nonsteroidal anti inflammatory drugs (such as diclofenac, indomethacin, ketoprofen, felbinac, loxoprofen, ibuprofen, flurbiprofen, tiaprofen, acemetacin, sulindac, etodolac, tolmetin, piroxicam, meloxicam, ampiroxicam, naproxen, azapropazone, methyl salicylate, glycol salicylate, valdecoxib, celecoxib, rofecoxib, and amfenac), antihistamine drugs (such as diphenhydramine, chlorpheniramine, mequitazine, and homochlorcyclizine), antihypertensive drugs (such as diltiazem, nicardipine, nilvadipine, metoprolol, bisoprolol, and trandolapril), antiparkinson drugs (such as pergolide, bromocriptine, ropinirole, and selegiline), bronchodilators (such as tulobuterol, isoproterenol, and salbutamol), antiallergic drugs (such as ketotifen, loratadine, azelastine, terfenadine, cetirizine, and acitazanolast), local anesthetics (such as lidocaine and dibucaine), narcotic analgesics (such as morphine), urological drugs (such as oxybutynin and tamsulosin), psychotropic agents (such as promazine and chlorpromazine), steroid hormone agents (such as estradiol, progesterone, norethisterone, cortisone, and hydrocortisone), antidepressants (such as sertraline, fluoxetine, paroxetine, and citalopram), antidementia drugs (such as donepezil, risperidone, rivastigmine, galantamine, and idebenone), expectorants (such as ambroxol), anti-anxiety drugs (such as tandospirone), antipsychotic drugs (such as olanzapine), central nervous system stimulants (such as methylphenidate), osteoporosis drugs (such as raloxifene and alendronate), breast cancer preventing drugs (such as tamoxifen), antiobesity drugs (such as mazindol and sibutramine), insomnia remedies (such as melatonin), and anti-rheumatic drugs (such as actarit).

The above drugs may be used alone or may be used in combination of two or more of them. In addition, the above drugs may be in the form of pharmaceutically acceptable salts. The content of the above drug is not particularly limited, and the drug may be blended as needed depending on the purpose. In general, however, the content of the drug based on the total mass of the adhesive layer (the content of the adhesive base agent is the solid content) is 0.1 to 70% by mass preferably, 1 to 50% by mass more preferably, and 3 to 30% by mass even more preferably.

In the patch of the present invention, the aforementioned adhesive layer may further comprise an additive ingredient such as a tackifier, a plasticizer, a transdermal absorption enhancer, a filler, or a stabilizer.

In the present invention, a tackifier that can be blended in the aforementioned adhesive layer may be any tackifier not particularly limited as far as the tackifier is generally usable in a patch, and examples thereof include: rosin, rosin derivatives such as rosin glycerol esters, hydrogenated rosin, hydrogenated rosin glycerol esters, rosin pentaerythritol esters; alicyclic saturated hydrocarbon resins such as Alcon P100 (trade name, Arakawa Chemical Industries, Ltd.); aliphatic hydrocarbon resins such as Quintone B170 (trade name, Zeon Corporation); terpene resins such as Clearon P-125 (trade name, YASUHARA CHEMICAL CO., LTD.); maleic acid copolymer resins, and the like. Among these, hydrogenated rosin glycerol esters, alicyclic saturated hydrocarbon resins, aliphatic hydrocarbon resins, and terpene resins are preferable.

The above tackifiers may be used alone or may be used in combination of two or more of them. Containing such tackifier(s), the obtained adhesive layer achieves more improved adhesiveness, and tends to maintain the other properties stably. The content of the aforementioned tackifier is not particularly limited, but is preferably 70% by mass or less, and more preferably 10 to 60% by mass, in general, based on the total mass of the adhesive layer (the content of the adhesive base agent is the solid content).

In the present invention, a plasticizer that can be blended in the aforementioned adhesive layer is not particularly limited, and any plasticizer may be blended as needed depending on the adhesive base agent used. Examples thereof include: petroleum-based oils such as paraffin oil (liquid paraffin), naphthene oil, and aromatic oil; animal oils such as squalane and squalene; vegetable oils such as olive oil, camellia oil, castor oil, tall oil, and peanut oil; dibasic acid esters such as dibutylphthalate and dioctyl phthalate; liquid rubbers such as polybutene (liquid polybutene) and liquid isoprene rubber; liquid fatty acid esters such as isopropyl palmitate, isopropyl myristate, hexyl laurate, diethyl sebacate, and diisopropyl sebacate; diethylene glycol; polyethylene glycol; glycol salicylate; propylene glycol; dipropylene glycol; triacetin; triethyl citrate; crotamiton; and the like. Among these, liquid paraffin, liquid polybutene, isopropyl palmitate, isopropyl myristate, diethyl sebacate, and hexyl laurate are preferable, and liquid polybutene, isopropyl palmitate, isopropyl myristate, and liquid paraffin are particularly preferable.

The above plasticizers may be used alone or may be used in combination of two or more of them. The content of the above plasticizer is not particularly limited, but is 60% by mass or less preferably, 0.5 to 50% by mass more preferably, 1 to 40% by mass even more preferably, and 2 to 30% by mass particularly preferably, in general, based on the total mass of the adhesive layer (the content of the adhesive base agent is the solid content).

In the present invention, a transdermal absorption enhancer that can be blended in the aforementioned adhesive layer is not particularly limited, and any transdermal absorption enhancer may be blended as needed depending on a drug to be used. Examples of such transdermal absorption enhancers include organic acids, fatty acids having a carbon chain of 6 to 20 carbon atoms, aliphatic alcohols having a carbon chain of 6 to 20 carbon atoms, fatty acid esters having a carbon chain of 6 to 20 carbon atoms, amides, ethers, aromatic organic acids, aromatic alcohols, aromatic organic acid esters and ethers (the above-listed substances may be either saturated or unsaturated and may be cyclic, linear, or branched), lactate esters, acetate esters, monoterpene-based compounds, sesquiterpene-based compounds, azone, azone derivatives, pirotiodecane, glycerol fatty acid esters, propylene glycol fatty acid esters, sorbitan fatty acid esters, polysorbates, polyethylene glycol fatty acid esters, polyoxyethylene hardened castor oils, polyoxyethylene alkyl ethers, sucrose fatty acid esters, vegetable oils, and the like. From the viewpoint of having a high solubility of a drug and accordingly a tendency to more surely prevent crystal precipitation, fatty acids having a carbon chain of 6 to 20 carbon atoms and aliphatic alcohols having a carbon chain of 6 to 20 carbon atoms are preferable, and fatty acids having a carbon chain of 6 to 20 carbon atoms are more preferable.

Specific examples of such transdermal absorption enhancers include lauric acid, myristic acid, palmitic acid, stearic acid, isostearic acid, oleic acid, linoleic acid, linolenic acid, lauryl alcohol, myristyl alcohol, oleyl alcohol, isostearyl alcohol, cetyl alcohol, octyldodecanol, methyl laurate, hexyl laurate, lauric diethanolamide, isopropyl myristate, myristyl myristate, octyldodecyl myristate, cetyl palmitate, methyl salicylate, ethyleneglycol salicylate, triethyl citrate, cetyl lactate, lauryl lactate, ethyl acetate, propyl acetate, geraniol, thymol, eugenol, terpineol, 1-menthol, borneolol, d-limonene, isoeugenol, isoborneol, nerol, dl-camphor, glycerol monocaprylate, glycerol monocaprate, glycerol monolaurate, glyceryl monooleate, sorbitan monolaurate, sucrose monolaurate, polysorbate 20, propylene glycol, propylene glycol monolaurate, polyethylene glycol monolaurate, polyethylene glycol monostearate, polyoxyethylene lauryl ether, polysorbate 20, polysorbate 60, polysorbate 80, pirotiodecane, olive oil, and the like.

The above transdermal absorption enhancers may be used alone or may be used in combination of two or more of them. The content of the above transdermal absorption enhancer is not particularly limited, but is 30% by mass or less preferably, 0.5 to 15% by mass more preferably, and 2 to 10% by mass even more preferably, in general, based on the total mass of the adhesive layer (the content of the adhesive base agent is the solid content).

In the present invention, a stabilizer that can be blended in the aforementioned adhesive layer is not particularly limited, and any stabilizer may be blended as needed depending on a drug to be used and other additive ingredients. Examples thereof include: antioxidants (such as tocopherol derivatives, ascorbic acid derivatives, erythorbic acid derivatives, nordihydroguaiaretic acid, gallic acid derivatives, dibutylhydroxytoluene (BHT), butylhydroxyanisole, sodium pyrosulfite, and sodium sulfite), ultraviolet absorbers (such as imidazole derivatives, benzotriazole derivatives, p-aminobenzoic acid derivatives, anthranilic acid derivatives, salicylic acid derivatives, cinnamic acid derivatives, benzophenone derivatives, coumaric acid derivatives, and camphor derivatives), and the like.

In addition, in the present invention, a filler that can be blended in the aforementioned adhesive layer is not particularly limited, and examples thereof include calcium carbonate, magnesium carbonate, silicate, cellulose derivatives (such as hydroxypropylcellulose, hydroxypropylmethylcellulose, and carboxymethyl cellulose), and the like.

Here, in the patch of the present invention, the thickness of the aforementioned adhesive layer is not particularly limited, but in general is 50 to 500 μm preferably, and 50 to 300 μm more preferably.

In the patch of the present invention, the opposite surface of the aforementioned adhesive layer from the backing is covered with the release liner. Such release liner is a release film for covering and protecting the adhesive layer, and may be any release liner not particularly limited as far as the release liner is generally usable in a patch. Such release liners are made of materials including, for example, resin films of polyesters (such as polyethylene terephthalate, polyethylene naphthalate, and polybutylene terephthalate), polyolefins (such as polyethylene and polypropylene), and the like; paper; cellulose derivatives; and the like. A material in which a surface to be in contact with the adhesive layer is release-treated by coating of silicone, Teflon (registered trademark), or the like is preferable, and a silicone-treated polyethylene terephthalate film is preferably used in particular.

A method for producing a patch of the present invention is not particularly limited except that the aforementioned nonfunctional silicone oil is blended in the process of obtaining the aforementioned adhesive layer. Thus, the patch of the present invention can be obtained by using a general method for producing a patch (a solvent method, a hot melt method, or the like). For example, the patch of the present invention can be obtained by: mixing and dissolving the nonfunctional silicone oil, the adhesive base agent, the drug (bioactive ingredient), the additive ingredient(s) and the like mentioned above with and in an organic solvent; applying the obtained adhesive solution to a release liner; thereafter removing the solvent by drying; stacking a backing on the adhesive layer thus formed; and then cutting the obtained patch sheet as needed.

EXAMPLES

Hereinafter, the present invention will be described more specifically based on Examples and Comparative Examples; however, the present invention is not limited to the following Examples.

Examples 1 and 2 and Comparative Examples 1 to 12

As specified in Tables 1 and 2 presented below, releasability improvers (nonfunctional silicone oil, polar silicone oil, polyvinylpyrrolidone, zinc oxide, glycinal, bentonite, kaolin, and talc), an adhesive base agent (acrylate ester-based copolymer), and additive ingredients (isopropyl palmitate (plasticizer) and oleic acid (transdermal absorption enhancer)) were used. These ingredients were measured out according to compositions specified in Tables 1 and 2 presented below and were mixed together into adhesive solutions. Then, each of the obtained adhesive solutions was applied onto a release liner (a PET film whose surface was release-treated with silicone), and the solvent was removed by drying to form an adhesive layer (the obtained adhesive layer has a thickness of 100 g/m$^2$). Subsequently, a backing (PET film) was stacked on the adhesive layer, which was then cut to obtain patches. Thereafter, the obtained patches were sealed and packaged in packaging bags made of an aluminum laminate film.

Note that the content in Tables 1 and 2 is a content (% by mass) based on the total mass of the adhesive layer, and the content of the adhesive base agent is a solid content. In addition, a blank cell in Tables 1 and 2 indicates that the content is 0 (zero).

TABLE 1

|  | Comp. Ex. 1 | Comp. Ex. 2 | Comp. Ex. 3 | Comp. Ex. 4 | Comp. Ex. 5 | Comp. Ex. 6 | Comp. Ex. 7 | Comp. Ex. 8 | Comp. Ex. 9 |
|---|---|---|---|---|---|---|---|---|---|
| Polyvinylpyrrolidone |  | 10 |  |  |  |  |  |  |  |
| Zinc Oxide |  |  | 1 | 3 |  |  |  |  |  |
| Glycinal (*1) |  |  |  |  | 1 | 3 |  |  |  |
| Bentonite |  |  |  |  |  |  | 10 |  |  |
| Kaolin |  |  |  |  |  |  |  | 10 |  |
| Talc |  |  |  |  |  |  |  |  | 10 |
| Acrylate Ester-based Copolymer (*2) | 90 | 80 | 89 | 87 | 89 | 87 | 80 | 80 | 80 |
| Isopropyl Palmitate (IPP) | 3 | 3 | 3 | 3 | 3 | 3 | 3 | 3 | 3 |
| Oleic Acid | 7 | 7 | 7 | 7 | 7 | 7 | 7 | 7 | 7 |
| Total | 100 | 100 | 100 | 100 | 100 | 100 | 100 | 100 | 100 |

(*1) Dihydroxyaluminum aminoacetate, manufactured by Kyowa Chemical Industry Co., Ltd.
(*2) Organic solvent solution of self-crosslinking type pressure-sensitive adhesive of copolymer of acrylate ester and vinyl acetate having alcoholic hydroxyl group, manufactured by Henkel AG & Co. KGaA, Product Name: DURO-TAK 87-2516

TABLE 2

|  | Ex. 1 | Ex. 2 | Comp. Ex. 10 | Comp. Ex. 11 | Comp. Ex. 12 |
|---|---|---|---|---|---|
| Nonfunctional Silicone Oil (*3) (Kinematic Viscosity of 20 cSt at 25° C.) | 2 | | | | |
| Nonfunctional Silicone Oil (*3) (Kinematic Viscosity of 350 cSt at 25° C.) | | 2 | | | |
| Nonfunctional Silicone Oil (*3) (Kinematic Viscosity of 1000 cSt at 25° C.) | | | 2 | | |
| Polar Silicone Oil (*4) (Kinematic Viscosity of 150 cSt at 25° C.) | | | | 2 | |
| Polar Silicone Oil (*5) (Kinematic Viscosity of 530 cSt at 25° C.) | | | | | 2 |
| Acrylate Ester-based Copolymer (*2) | 88 | 88 | 88 | 88 | 88 |
| Isopropyl Palmitate (IPP) | 3 | 3 | 3 | 3 | 3 |
| Oleic Acid | 7 | 7 | 7 | 7 | 7 |
| Total | 100 | 100 | 100 | 100 | 100 |

(*2) Organic solvent solution of self-crosslinking type pressure-sensitive adhesive of copolymer of acrylate ester and vinyl acetate having alcoholic hydroxyl group, manufactured by Henkel AG & Co. KGaA, Product Name: DURO-TAK 87-2516
(*3) Dimethylpolysiloxane
(*4) PEG-3 Dimethicone, polyether modified silicone oil with HLB 4.5
(*5) PEG-10 Dimethicone, polyether modified silicone oil with HLB 14.5

Using the patches obtained, "release liner peel test" and "bleeding prevention test" were conducted in accordance with the methods described below. Tables 3 and 4 present the obtained results.

bled out on the surface of each patch was evaluated based on the following criteria:
A: No bleeding is observed (pass);
B: Slight bleeding is observed (quasi-pass); and
C: Noticeable bleeding is observed (fail).

TABLE 3

| | | Comp. Ex. 1 | Comp. Ex. 2 | Comp. Ex. 3 | Comp. Ex. 4 | Comp. Ex. 5 | Comp. Ex. 6 | Comp. Ex. 7 | Comp. Ex. 8 | Comp. Ex. 9 |
|---|---|---|---|---|---|---|---|---|---|---|
| Releasablity of Release Liner | Initial | 3 | 3 | 3 | 3 | 3 | 3 | 3 | 3 | 3 |
| | 60° C./1 W | 5 | 5 | 5 | 5 | 5 | 5 | 5 | 5 | 5 |
| Bleeding Prevention | Initial | A | A | A | A | A | A | A | A | A |
| | 60° C./1 W | A | A | A | A | A | A | A | A | A |

<Release Liner Peel Test>

Using each patch before being sealed in the aforementioned packaging bag (Initial) and each patch taken out by opening the aforementioned packaging bag after one-week storage in a chamber at 60° C. (60° C./1 W), easiness of peeling-off in removing the release liner from the patch (the strength of a force required to peel off) was evaluated based on following criteria:
1: the release liner moves out of alignment with the adhesive layer (fail);
2: the release liner can be peeled off with a light force, but sometimes moves out of alignment with the adhesive layer (fail);
3: the release liner remains in alignment with the adhesive layer and can be peeled off with a moderate force (pass);
4: the release liner remains in alignment with the adhesive layer, but requires a slightly strong force for peeling-off (quasi-pass); and
5: the release liner remains in alignment with the adhesive layer, but requires a very strong force for peeling-off (fail).

<Bleeding Prevention Test>

Using each patch before being sealed in the aforementioned packaging bag (Initial) and each patch taken out by opening the aforementioned packaging bag after one-week storage in the chamber at 60° C. (60° C./1 W), the release liners were removed from the patches. Then, whether liquid

TABLE 4

| | | Ex. 1 | Ex. 2 | Comp. Ex. 10 | Comp. Ex. 11 | Comp. Ex. 12 |
|---|---|---|---|---|---|---|
| Releasablity of Release Liner | Initial | 3 | 3 | 3 | 3 | 3 |
| | 60° C./1 W | 3 | 4 | 5 | 5 | 5 |
| Bleeding Prevention | Initial | A | A | A | A | A |
| | 60° C./1 W | A | A | A | A | A |

As is apparent from the results presented in Tables 3 and 4, the patches obtained in Examples 1, 2 in which the nonfunctional silicone oil according to the present invention was blended caused no bleeding, and improvement in the releasability thereof was observed. The results demonstrated that the patches in Example 1, in particular, had adequate releasability of the release liner, and maintained the adequate releasability stably over time.

On the other hand, as for the patches obtained in Comparative Example 1 in which any releasability improver was not blended, the release liner became very difficult to peel off due to an aging deterioration of the releasability. Meanwhile, as for the patches obtained in Comparative Examples 2, 3, 5, and 7 to 9 in which the conventional releasability improvers were blended, the releasability deteriorated over time and almost no improvement in the releasability was observed. Moreover, also as for the patches obtained in Comparative Examples 4 and 6 in which the contents of the conventional releasability improvers were increased, the releasability deteriorated over time and almost no improvement in the releasability was observed.

Then, as for the patches obtained in Comparative Example 10 in which the nonfunctional silicone oil having a higher kinematic viscosity than that according to the present invention was blended, and the patches obtained in Comparative Examples 11 and 12 in which the silicone oils containing polar functional groups were blended, the releasability deteriorated over time and almost no improvement in the releasability was observed.

Example 3 and Comparative Example 13

Patches were obtained and sealed in packaging bags in the same manner as in Example 1 except for use of adhesive solutions obtained by using, as specified in Table 5 presented below, a releasability improver (nonfunctional silicone oil), adhesive base agents (styrene-isoprene-styrene block copolymer and polyisobutylene), and additive ingredients (alicyclic saturated hydrocarbon resin (tackifier), liquid paraffin (plasticizer), isopropyl palmitate (plasticizer), and octyldodecanol (transdermal absorption enhancer)), in such a way that these ingredients were measured out according to compositions specified in Table 5 presented below and were dissolved in a solvent (toluene). Also, the content in Table 5 is a content (% by mass) based on the total mass of the adhesive layer, and the content of the adhesive base agent is a solid content.

Using the patches obtained, the "release liner peel test" and the "bleeding prevention test" were conducted in accordance with the aforementioned methods. Table 6 presents the obtained results.

TABLE 5

|  | Comp. Ex. 13 | Ex. 3 |
|---|---|---|
| Nonfunctional Silicone Oil (*3) (Kinematic Viscosity Of 20 cSt at 25° C.) | 0 | 0.3 |
| Styrene-Isoprene-Styrene Block Copolymer (SIS) | 17.5 | 17.4 |
| Polyisobutylene (PIB) | 7.5 | 7.5 |
| Alicyclic Saturated Hydrocarbon Resin | 50 | 49.8 |
| Liquid Paraffin | 10 | 10 |
| Isopropyl Palmitate (IPP) | 10 | 10 |
| Octyldodecanol | 3 | 3 |
| Other Ingredient | 2 | 2 |
| Total | 100 | 100 |

(*3) Dimethylpolysiloxane

TABLE 6

|  |  | Comp. Ex. 13 | Ex. 3 |
|---|---|---|---|
| Releasablity of Release Liner | Initial | 3 | 3 |
|  | 60° C./1 W | 5 | 3 |
| Bleeding Prevention | Initial | A | A |
|  | 60° C./1 W | A | A |

As is apparent from the results presented in Table 6, the patches obtained in Example 3 in which the nonfunctional silicone oil according to the present invention was blended caused no bleeding, and improvement in the releasability thereof was observed, which demonstrated that the patches had adequate releasability of the release liner, and maintained the adequate releasability stably over time. On the other hand, as for the patches obtained in Comparative Example 13 in which any releasability improver was not blended, the release liner became very difficult to peel off due to an aging deterioration of the releasability.

Examples 4 to 8 and Comparative Examples 14 and 15

Patches were obtained and sealed in packaging bags in the same manner as in Example 1 except for use of adhesive solutions obtained by using, as specified in Table 7 presented below, a releasability improver (nonfunctional silicone oil), an adhesive base agent (acrylate ester-based copolymer), and additive ingredients (isopropyl palmitate (plasticizer) and oleic acid (transdermal absorption enhancer)), in such a way that these ingredients were measured out according to compositions specified in Table 7 presented below and were mixed together. Also, the content in Table 7 is a content (% by mass) based on the total mass of the adhesive layer, and the content of the adhesive base agent is a solid content.

Using the patches obtained, the "release liner peel test" and the "bleeding prevention test" were conducted in accordance with the aforementioned methods. Table 8 presents the obtained results.

TABLE 7

|  | Comp. Ex. 1 | Comp. Ex. 14 | Ex. 4 | Ex. 5 | Ex. 6 | Ex. 7 | Ex. 8 | Comp. Ex. 15 |
|---|---|---|---|---|---|---|---|---|
| Nonfunctional Silicone Oil (*3) (Kinematic Viscosity of 20 cSt at 25° C.) | 0 | 0.1 | 0.3 | 0.5 | 1 | 3 | 5 | 10 |
| Acrylate Ester-based Copolymer (*2) | 90 | 89.9 | 89.7 | 89.5 | 89 | 88 | 85 | 80 |
| Isopropyl Palmitate (IPP) | 3 | 3 | 3 | 3 | 3 | 3 | 3 | 3 |
| Oleic Acid | 7 | 7 | 7 | 7 | 7 | 7 | 7 | 7 |
| Total | 100 | 100 | 100 | 100 | 100 | 100 | 100 | 100 |

(*2) Organic solvent solution of self-crosslinking type pressure-sensitive adhesive of copolymer of acrylate ester and vinyl acetate having alcoholic hydroxyl group, manufactured by Henkel AG & Co. KGaA, Product Name: DURO-TAK 87-2516
(*3) Dimethylpolyslioxane

TABLE 8

|  |  | Comp. Ex. 1 | Comp. Ex. 14 | Ex. 4 | Ex. 5 | Ex. 6 | Ex. 7 | Ex. 8 | Comp. Ex. 15 |
|---|---|---|---|---|---|---|---|---|---|
| Releasablity of Release Liner | Initial | 3 | 3 | 3 | 3 | 3 | 3 | 3 | 2 |
|  | 60° C./1 W | 5 | 5 | 3 | 3 | 3 | 3 | 3 | 2 |
| Bleeding Prevention | Initial | A | A | A | A | A | A | B | C |
|  | 60° C./1 W | A | A | A | A | A | A | B | C |

As is apparent from the results presented in Table 8, the patches obtained in Examples 4 to 8 in each of which the nonfunctional silicone oil according to the present invention was blended to have a content specified in the present invention caused no bleeding (but slight bleeding occurred in the patches obtained in Example 8), and improvement in the releasability thereof was observed, which demonstrated that the patches had adequate releasability of the release liner, and maintained the adequate releasability stably over time. On the other hand, as for the patches obtained in Comparative Example 14 in which the content of the nonfunctional silicone oil was less than the content specified in the present invention, slight improvement in the releasability was observed, but the effect was insufficient because the releasability deteriorated over time. Meanwhile, the patches obtained in Comparative Example 15 in which the content of the nonfunctional silicone oil was more than the content specified in the present invention scored "fail" because noticeable bleeding occurred, the adhesiveness to the skin was poor, and the release liner moved out of alignment with the adhesive layer in some cases.

Examples 9 to 12 and Comparative Example 16

Patches were obtained and sealed in packaging bags in the same manner as in Example 1 except for use of adhesive solutions obtained by using, as specified in Table 9 presented below, a releasability improver (nonfunctional silicone oil), an adhesive base agent (acrylate ester-based copolymer), and additive ingredients (isopropyl palmitate (plasticizer) and oleic acid (transdermal absorption enhancer)), in such a way that these ingredients were measured out according to compositions specified in Table 9 presented below and were mixed together. Also, the content in Table 9 is a content (% by mass) based on the total mass of the adhesive layer, and the content of the adhesive base agent is a solid content. In addition, a blank cell in Table 9 indicates that the content is 0 (zero).

Using the patches obtained, the "release liner peel test" and the "bleeding prevention test" were conducted in accordance with the aforementioned methods. Table 10 presents the obtained results.

TABLE 9

| | Comp. Ex. 16 | Ex. 1 | Ex. 9 | Ex. 10 | Ex. 11 | Ex. 12 | Ex. 2 | Comp. Ex. 10 |
|---|---|---|---|---|---|---|---|---|
| Nonfunctional Silicone Oil (*3) (Kinematic Viscosity of 5 cSt at 25° C.) | 2 | | | | | | | |
| Nonfunctional Silicone Oil (*3) (Kinematic Viscosity of 20 cSt at 25° C.) | | 2 | | | | | | |
| Nonfunctional Silicone Oil (*3) (Kinematic Viscosity of 30 cSt at 25° C.) | | | 2 | | | | | |
| Nonfunctional Silicone Oil (*3) (Kinematic Viscosity of 50 cSt at 25° C.) | | | | 2 | | | | |
| Nonfunctional Silicone Oil (*3) (Kinematic Viscosity of 100 cSt at 25° C.) | | | | | 2 | | | |
| Nonfunctional Silicone Oil (*3) (Kinematic Viscosity of 200 cSt at 25° C.) | | | | | | 2 | | |
| Nonfunctional Silicone Oil (*3) (Kinematic Viscosity of 350 cSt at 25° C.) | | | | | | | 2 | |
| Nonfunctional Silicone Oil (*3) (Kinematic Viscosity of 1000 cSt at 25° C.) | | | | | | | | 2 |
| Acrylate Ester-based Copolymer (*2) | 88 | 88 | 88 | 88 | 88 | 88 | 88 | 88 |
| Isopropyl Palmitate (IPP) | 3 | 3 | 3 | 3 | 3 | 3 | 3 | 3 |
| Oleic Acid | 7 | 7 | 7 | 7 | 7 | 7 | 7 | 7 |
| Total | 100 | 100 | 100 | 100 | 100 | 100 | 100 | 100 |

(*2) Organic solvent solution of self-crosslinking type pressure-sensitive adhesive of copolymer of acrylate ester and vinyl acetate having alcoholic hydroxyl group, manufactured by Henkel AG & Co. KGaA, Product Name: DURO-TAK 87-2516
(*3) Dimethylpolysiloxne

TABLE 10

| | | Comp. Ex. 16 | Ex. 1 | Ex. 9 | Ex. 10 | Ex. 11 | Ex. 12 | Ex. 2 | Comp. Ex. 10 |
|---|---|---|---|---|---|---|---|---|---|
| Releasablity of Release Liner | Initial | 2 | 3 | 3 | 3 | 3 | 3 | 3 | 3 |
| | 60° C./1 W | 2 | 3 | 3 | 3 | 3 | 3 | 4 | 5 |
| Bleeding Prevention | Initial | A | A | A | A | A | A | A | A |
| | 60° C./1 W | A | A | A | A | A | A | A | A |

As is apparent from the results presented in Table 10, the patches obtained in Examples 1, 2, and 9 to 12 in each of which the nonfunctional silicone oil according to the present invention was blended caused no bleeding, and improvement in the releasability thereof was observed, which demonstrated that the patches had adequate releasability of the release liner, and maintained the adequate releasability stably over time. On the other hand, as for the patches obtained in Comparative Example 10 in which the nonfunctional silicone oil having a higher kinematic viscosity than that of the present invention was blended, the releasability deteriorated over time and almost no improvement in the releasability was observed. Meanwhile, the patches obtained in Comparative Example 16 in which the nonfunctional silicone oil having a lower kinematic viscosity than that of the present invention was blended scored "fail" because the release liner moved out of alignment with the adhesive layer in some cases although the release liner was able to be peeled off with a light force.

Examples 13 and 14 and Comparative Examples 17 and 18

Patches were obtained and sealed in packaging bags in the same manner as in Example 1 except for use of adhesive solutions obtained by using, as specified in Table 11 presented below, a drug (galantamine), a releasability improver (nonfunctional silicone oil), an adhesive base agent (acrylate ester-based copolymer), and additive ingredients (isopropyl palmitate (plasticizer) and oleic acid (transdermal absorption enhancer)), in such a way that these ingredients were measured out according to compositions specified in Table 11 presented below and were mixed together. Also, the content in Table 11 is a content (% by mass) based on the total mass of the adhesive layer, and the content of the adhesive base agent is a solid content.

Using the patches obtained, the "release liner peel test" and the "bleeding prevention test" were conducted in accordance with the aforementioned methods. Table 12 presents the obtained results.

TABLE 11

|  | Comp. Ex. 17 | Comp. Ex. 18 | Ex. 13 | Ex. 14 |
|---|---|---|---|---|
| Galantamine | 7.8 | 7.8 | 7.8 | 7.8 |
| Nonfunctional Silicone Oil (*3) (Kinematic Viscosity of 20 cSt at 25° C.) | 0 | 0.1 | 1 | 5 |
| Acrylate Ester-based Copolymer (*2) | 82.2 | 82.1 | 81.2 | 77.2 |
| Isopropyl Palmitate (IPP) | 3 | 3 | 3 | 3 |
| Oleic Acid | 7 | 7 | 7 | 7 |
| Total | 100 | 100 | 100 | 100 |

(*2) Organic solvent solution of self-crosslinking type pressure-sensitive adhesive of copolymer of acrylate ester and vinyl acetate having alcoholic hydroxyl group, manufactured by Henkel AG & Co. KGaA, Product Name: DURO-TAK 87-2516
(*3) Dimethylpolysiloxane

TABLE 12

|  |  | Comp. Ex. 17 | Comp. Ex. 18 | Ex. 13 | Ex. 14 |
|---|---|---|---|---|---|
| Releasability of Release Liner | Initial | 3 | 3 | 3 | 3 |
|  | 60° C./1 W | 5 | 5 | 3 | 3 |
| Bleeding Prevention | Initial | A | A | A | B |
|  | 60° C./1 W | A | A | A | B |

As is apparent from the results presented in Table 12, the patches obtained in Examples 13 and 14 in each of which the nonfunctional silicone oil according to the present invention was blended to have a content specified in the present invention caused no bleeding (but slight bleeding occurred in the patches obtained in Example 14), and improvement in the releasability thereof was observed, which demonstrated that the patches had adequate releasability of the release liner, and maintained the adequate releasability stably over time. On the other hand, as for the patches obtained in Comparative Example 17 in which any nonfunctional silicone oil was not blended, the release liner became very difficult to peel off due to an aging deterioration of the releasability. Meanwhile, as for the patches obtained in Comparative Example 18 in which the content of the nonfunctional silicone oil was less than the content specified in the present invention, slight improvement in the releasability was observed, but the effect was insufficient because the releasability deteriorated over time.

Subsequently, using the patches obtained in Example 13, "skin adhesion test", "transdermal absorbability test" and "drug temporal stability test" were conducted in accordance with the methods described below. Then, no problem was found in any of the test results, which demonstrated that the patches of the present invention achieved the adjustment of the releasability from the release liner to the adequate range and obtained the ability to maintain the adequate releasability stably over time while having no adverse effects on the adhesiveness to the skin and the transdermal absorbability (skin permeability) and temporal stability of the drug contained therein.

<Skin Adhesion Test>
Each patch was peeled off from the release liner, the thumb was pressed against the surface of the adhesive layer, and the cohesive strength and adhesive strength of the patch exerted in the course of moving the thumb off the surface were evaluated. In addition, each patch was attached to the stratum corneum side of the human skin (at the abdomen) for testing, and then was peeled off after storage at 32±1° C. for 3 hours. Thus, the peeling resistance in the peeling was evaluated.

<Transdermal Absorbability Test>
The skin (at a side of the trunk) which was peeled off from hairless mice of 7 to 10 weeks old and from which the fat was removed, or the human skin (at the abdomen) for testing which was cut (by a dermatome) with a thickness of about 500 μm from the stratum corneum side was used. Each patch (3 cm$^2$) was attached to the stratum corneum side of the skin, and the resultant skin was set in a flow-through diffusion cell with the dermis side of the skin placed on the receptor chamber side. A phosphate buffered saline of pH 7.4 was used on the receptor chamber side and warm water was circulated around the outer periphery of the cell such that the surface of the skin was at a temperature of 32±1° C. The flow rate of the receptor solution was set at a rate of 2.5 mL/hr and the receptor solution was sampled every 4 hours. Of the receptor solution obtained at each sampling point, the fluid volume was exactly measured, and the drug concentration was also measured by high performance liquid chromatography. Hence, the permeation rate of the drug per hour for each patch was calculated based on the measured values of the fluid volume and the drug concentration.

<Drug Temporal Stability Test>
Each patch was cut into a size of 6.25 cm$^2$ to obtain samples to be used in the test. The value of a content ($N_i$) of the drug obtained by measurement of each sample stored for two weeks or one month in a thermo-hygrostat at a temperature of 60° C. and a humidity of 75% and the value of a content ($N_0$) of the drug obtained by measurement of the initial sample were assigned into the following relational expression (1):

$$R_i(\%) = (N_i/N_0) \times 100 \quad (1).$$

The value ($R_i$) thus obtained was taken as a ratio (%) of the post-storage content to the initial content of the drug of each sample under the above-specified conditions.

Here, the content of the drug was determined by the following method. Specifically, first, the release liner was peeled off from each patch, and the patch was placed in a 50 mL centrifuge tube. Next, 10 mL of a hydrochloric acid-methanol solution was put as an extract solution in the 50 mL centrifuge tube, followed by shaking for 1 hour. Then, an internal standard substance (methyl p-hydroxybenzoate/(hydrochloric acid-methanol solution)) was added, and the resultant mixture was diluted to 50 mL in total with a water-methanol solution, followed by shaking for 30 minutes. Each sample thus prepared was analyzed by high performance liquid chromatography to determine the content of the drug.

Examples 15 to 32

The "release liner peel test" and the "bleeding prevention test" were conducted in accordance with the aforementioned methods using patches obtained in the same manner as in Example 13 except that indomethacin (Example 15), ketoprofen (Example 16), felbinac (Example 17), methyl salicylate (Example 18), glycol salicylate (Example 19), bisoprolol (Example 20), pergolide (Example 21), ropinirole (Example 22), tulobuterol (Example 23), ketotifen (Example 24), lidocaine (Example 25), oxybutynin (Example 26), tamsulosin (Example 27), asenapine (Example 28), estradiol (Example 29), risperidone (Example 30), rivastigmine (Example 31), and methylphenidate (Example 32) were used as drugs.

As a result, in all the patches, no bleeding occurred and improvement in the releasability was observed, which demonstrated that the patches had adequate releasability of the release liner, and maintained the adequate releasability stably over time.

INDUSTRIAL APPLICABILITY

As has been described above, according to the present invention, in a patch in which an adhesive layer and a release liner are laminated on at least one surface of a backing, it is possible to adjust the releasability from the release liner to an adequate range and to maintain the adequate releasability stably over time without changing the basic composition of the adhesive layer containing an acrylate-based adhesive or a rubber-based adhesive as an adhesive base agent, while having no adverse effects on the adhesiveness to the skin and the transdermal absorbability (skin permeability) and the temporal stability of a drug to be contained therein.

Therefore, for the development of various kinds of patches each including an adhesive layer containing an acrylate-based adhesive or a rubber-based adhesive as an adhesive base agent, the present invention is very useful as a technique for adjusting the releasability from a release liner to an adequate range and maintaining the adequate releasability stably over time without changing the basic composition of the adhesive layer.

The invention claimed is:

1. A patch comprising an adhesive layer and a release liner laminated on at least one surface of a backing, wherein
the adhesive layer comprises, as an adhesive base agent, at least one selected from the group consisting of acrylate-based adhesives and rubber-based adhesives,
the adhesive layer comprises, as a plasticizer, at least one selected from the group consisting of liquid paraffin, liquid polybutene, isopropyl palmitate, isopropyl myristate, diethyl sebacate, and hexyl laurate,
the adhesive layer comprises, as a transdermal absorption enhancer, at least one selected from the group consisting of fatty acids having a carbon chain of 6 to 20 carbon atoms and aliphatic alcohols having a carbon chain of 6 to 20 carbon atoms, and
the adhesive layer comprises 0.3 to 3% by mass of a nonfunctional silicone oil having a kinematic viscosity of 20 to 250 cSt at 25° C. wherein the nonfunctional silicone oil is at least one selected from the group consisting of dimethylpolysiloxane and methylphenylpolysiloxane.

2. The patch according to claim 1, wherein
the adhesive layer further comprises a drug.

3. The patch according to claim 1, wherein
the adhesive layer further comprises, as a tackifier, at least one selected from the group consisting of hydrogenated rosin glycerol esters, alicyclic saturated hydrocarbon resins, aliphatic hydrocarbon resins, and terpene resins.

4. The patch according to claim 1, wherein
the adhesive base agent is an acrylate ester-based copolymer, and
the adhesive layer further comprises a liquid fatty acid ester and a fatty acid having a carbon chain of 6 to 20 carbon atoms.

5. The patch according to claim 1, wherein
the adhesive base agent comprises a styrene-isoprene-styrene block copolymer and polyisobutylene, and
the adhesive layer further comprises an alicyclic saturated hydrocarbon resin, a petroleum-based oil, a liquid fatty acid ester, and an aliphatic alcohol having a carbon chain of 6 to 20 carbon atoms.

* * * * *